(12) United States Patent
Liu et al.

(10) Patent No.: US 8,674,086 B2
(45) Date of Patent: Mar. 18, 2014

(54) NUCLEOTIDES AND OLIGONUCLEOTIDES FOR NUCLEIC ACID SEQUENCING

(75) Inventors: Jianquan Liu, Fremont, CA (US); Xing Su, Cupertino, CA (US); Kai Wu, Mountain View, CA (US)

(73) Assignee: Intel Corporation, Santa Clara, CA (US)

( * ) Notice: Subject to any disclaimer, the term of this patent is extended or adjusted under 35 U.S.C. 154(b) by 592 days.

(21) Appl. No.: 12/823,995

(22) Filed: Jun. 25, 2010

(65) Prior Publication Data
US 2011/0319276 A1    Dec. 29, 2011

(51) Int. Cl.
*C07H 19/20* (2006.01)
*C07H 19/00* (2006.01)
*C07H 19/04* (2006.01)

(52) U.S. Cl.
USPC ............... 536/26.2; 536/26.21; 536/26.22; 536/26.3

(58) Field of Classification Search
None
See application file for complete search history.

(56) References Cited

U.S. PATENT DOCUMENTS

| | | | |
|---|---|---|---|
| 5,849,487 | A | 12/1998 | Hase |
| 2006/0199193 | A1 | 9/2006 | Koo et al. |
| 2009/0170716 | A1 | 7/2009 | Su et al. |
| 2010/0167938 | A1 | 7/2010 | Su et al. |

OTHER PUBLICATIONS

Rensland et al., Biochemistry, 1995, 34, pp. 593-599.*
Koo et al., U.S. Appl. No. 11/073,160, entitled "Sensor Arrays and Nucleic Acid Sequencing Applications," filed Mar. 4, 2005, 31 pages.
Su et al., U.S. Appl. No. 12/459,309, entitled "Chemically Induced Optical Signals and DNA Sequencing," filed Jun. 30, 2009, 45 pages.
Elibol et al., U.S. Appl. No. 12/655,578, entitled "Nanogap Chemical and Biochemical Sensors," filed Dec. 31, 2009, 49 pages.
Peng et al., "Polymerase-Directed Synthesis of 2'-Deoxy-2'-fluoro-β-D-arabinonucleic Acids," Journal of American Chemical Society, vol. 129, No. 17, Apr. 10, 2007, pp. 5310-5311.
Watts et al., "2'F-Arabinonucleic acids (2'F-ANA)—History, properties, and new frontiers," Canadian Journal of Chemistry, vol. 86, No. 7, Jul. 1, 2008, pp. 641-656.
Bentley et al., "Accurate whole human genome sequencing using reversible terminator chemistry," Nature, vol. 456, Nov. 6, 2008, pp. 53-59.
Elibol et al., "Nanoscale thickness double-gated field effect silicon sensors for sensitive pH detection in fluid," Applied Physics Letters, vol. 92, No. 19, May 2008, pp. 193904-1 to 193904-3.
Gabig-Ciminska et al., "Electric chips for rapid detection and quantification of nucleic acids," Biosensors and Bioelectronics, vol. 19, 2004, pp. 537-546.
Guo et al., "Four-color DNA sequencing with 3'-O-modified nucleotide reversible terminators and chemically cleavable fluorescent dideoxynucleotides," Proceedings of the National Academy of Sciences (PNAS), vol. 105, No. 27, Jul. 8, 2008, pp. 9145-9150.
Kling, "Ultrafast DNA sequencing," Nature Biotechnology, Nature Publishing Group, vol. 21, No. 12, Dec. 2003, pp. 1425-1427.
Ronaghi et al., "DNA Sequencing: A Sequencing Method Based on Real-Time Pyrophosphate," Science Magazine, vol. 281, No. 5375, Jul. 17, 1998, pp. 363-365.
Seeberger et al., "2'-Deoxynucleoside Dithiophosphates: Synthesis and Biological Studies," Journal of American Chemical Society, vol. 117, No. 5, Feb. 1995, pp. 1472-1478.
Yeung et al., "Electrochemical Real-Time Polymerase Chain Reaction," Journal of American Chemical Society, vol. 128, No. 41, Sep. 23, 2006, 4 pages.

* cited by examiner

*Primary Examiner* — Traviss C McIntosh, III

(57) ABSTRACT

Embodiments of the invention provide non-natural bifunctional nucleotides having both nuclease resistance and nucleic acid synthesis blocking properties and methods of sequencing nucleic acids that employ non-natural bifunctional nucleic acids. Additional embodiments provide non-natural oligonucleotides and methods for sequencing nucleic acids using the non-natural oligonucleotides. Methods according to embodiments of the invention employ electronic detection and fluorescent detection of nucleic acid sequencing reactions.

14 Claims, 12 Drawing Sheets

NUCLEOTIDES AND OLIGONUCLEOTIDES FOR NUCLEIC ACID SEQUENCING

CROSS REFERENCE TO RELATED APPLICATIONS

The present application is related to U.S. patent application Ser. No. 11/226,696, entitled "Sensor Arrays and Nucleic Acid Sequencing Applications," filed Sep. 13, 2005, now pending, which is a continuation-in-part application that claims the benefit of U.S. patent application Ser. No. 11/073,160, entitled "Sensor Arrays and Nucleic Acid Sequencing Applications," filed Mar. 4, 2005, and is also related to U.S. patent application Ser. No. 11/967,600, entitled "Electronic Sensing for Nucleic Acid Sequencing," filed Dec. 31, 2007, U.S. patent application Ser. No. 12/319,168, entitled "Nucleic Acid Sequencing and Electronic Detection," filed Dec. 31, 2008, U.S. patent application Ser. No. 12/459,309, entitled "Chemically Induced Optical Signals," filed Jun. 30, 2009, now pending, and U.S. patent application Ser. No. 12/655,578, entitled "Nanogap Chemical and Biochemical Sensors," filed Dec. 31, 2009, now pending, the disclosures of which are incorporated herein by reference.

BACKGROUND OF THE INVENTION

1. Field of the Invention

Embodiments of the present invention relate generally to electronic sensors, electronic detection of nucleic acids, non-natural nucleotides and oligonucleotides, nucleic acid sequencing reactions, and nucleic acid sequencing.

2. Background Information

Genetic information in living organisms is contained in very long polymeric molecules known as nucleic acids. Typical nucleic acids are deoxyribonucleic acid (DNA) and ribonucleic acid (RNA). Naturally occurring DNA and RNA molecules are generally composed of four different chemical building blocks called nucleotides which are in turn made up of a sugar (deoxyribose or ribose, respectively), phosphoric acid, and one of five bases, adenine (A), cytosine (C), guanine (G), and thymine (T) or uracil (U). The human genome contains approximately three billion base pairs and an estimated 20,000 to 25,000 genes. A genome is all the genetic material in a cell's chromosomes. DNA sequence information can be used to determine multiple characteristics of an individual as well as the presence of and or suceptibility to many common diseases, such as cancer, cystic fibrosis, and sickle cell anemia. Further, knowledge of an individual's genome provides an opportunity to personalize medical treatments since it is known, for example, that certain drugs are only or are most effective in individuals having a specific genetic makeup. The effectiveness of newly discovered drugs can be mapped out based on genetics. As a result of genetic information, time wasted in an ineffective treatment and side effects from treatment(s) can be avoided for individuals whose genetic make up indicates that they will not benefit from a treatment. Determination of the entire three billion nucleotide sequence of the human genome has provided a foundation for identifying the genetic basis of diseases. The first determination of the entire sequence of the human genome required years to accomplish. The need for nucleic acid sequence information also exists in research, environmental protection, food safety, biodefense, and clinical applications, such as for example, pathogen detection, i.e., the detection of the presence or absence of pathogens or their genetic varients.

Thus, because DNA sequencing is an important technology for applications in bioscience such as the analysis of genetic information content for an organism, tools that allow for faster and or more reliable sequence determination are valuable. Applications such as, for example, population-based biodiversity projects, disease detection, personalized medicine, prediction of effectiveness of drugs, and genotyping using single-nucleotide polymorphisms, stimulate the need for simple and robust methods for sequencing short lengths of nucleic acids (such as those containing 1-20 bases). Sequencing methods that provide increased accuracy and or robustness, decreased need for analysis sample, and or high throughput are valuable analytical and biomedical tools.

Additionally, molecular detection platforms that are miniaturized and manufacturable in high volumes provide access to affordable disease detection to many people in places and situations in which such access was not in the past possible. The availability of affordable molecular diagnostic devices reduces the cost of and improves the quality of healthcare available to society. Additionally, portable molecular detection devices have applications in security and hazard detection and remediation fields and offer the ability to immediately respond appropriately to a perceived security or accidental biological or chemical hazard.

DETAILED DESCRIPTION OF THE INVENTION

Figure 1:
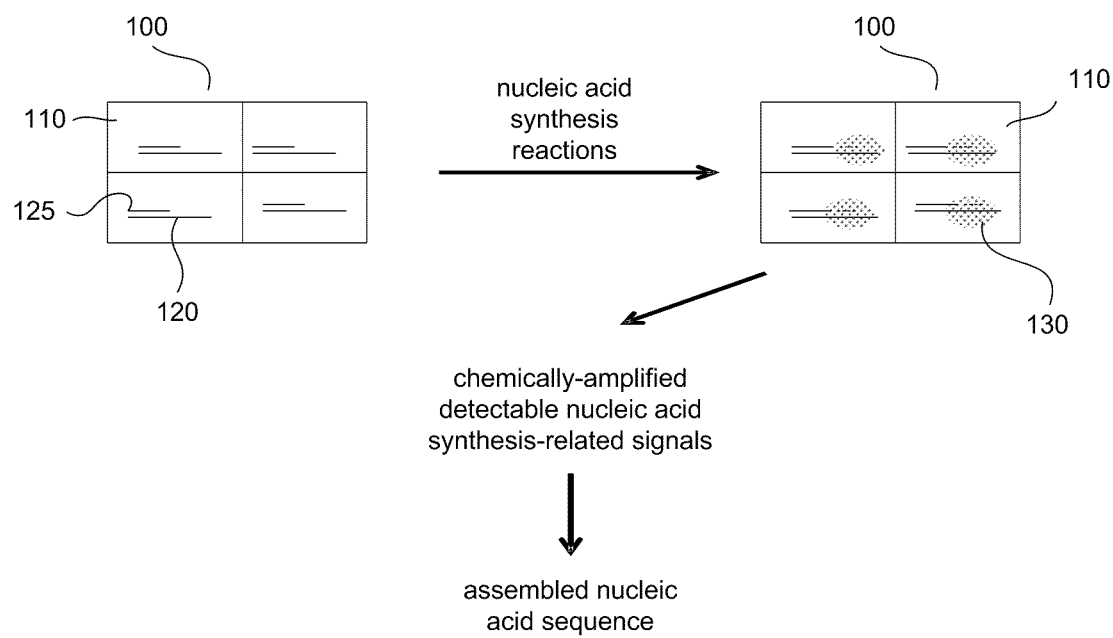
FIG. 1 provides a simplified diagram of a method for sequencing nucleic acids employing a sensor array to detect reaction products.

Embodiments of the present invention provide non-natural nucleic acids and oligonucleosides and methods for sequencing nucleic acids and nucleic acid detection. In general, nucleic acids (polynucleotides) that can be sequenced include polymers of deoxyribonucleotides (DNA) or ribonucleotides (RNA) and analogs thereof that are linked together by a phosphodiester bond. A polynucleotide can be a genome, a portion of a genome, a gene or a portion thereof, a cDNA, a synthetic polydeoxyribonucleic acid sequence, or RNA (ribonucleic acid). A polynucleotide, including an oligonucleotide (for example, a probe or a primer) can contain nucleoside or nucleotide analogs, or a backbone bond other than a phosphodiester bond. In general, the nucleotides in a polynucleotide are naturally occurring deoxyribonucleotides (or deoxyribonucleosides), such as adenine, cytosine, guanine or thymine linked to 2'-deoxyribose, or ribonucleotides (or ribonucleosides) such as adenine, cytosine, guanine or uracil linked to ribose. However, a polynucleotide or oligonucleotide also can contain nucleotide analogs, including non-naturally occurring synthetic nucleotides or modified naturally occurring nucleotides.

The covalent bond linking the nucleotides of a polynucleotide generally is a phosphodiester bond. However, the covalent bond also can be any of a number of other types of bonds, including a thiodiester bond, a phosphorothioate bond, a peptide-like amide bond or any other bond known to those in the art as useful for linking nucleotides (nucleosides) to produce synthetic polynucleotides. The incorporation of non-naturally occurring nucleotide analogs or bonds linking the nucleotides or analogs can be particularly useful where the polynucleotide is to be exposed to an environment that can contain nucleolytic activity (including endonuclease and exonuclease activity), since the modified polynucleotides can be less susceptible to degradation.

Virtually any naturally occurring nucleic acid may be sequenced including, for example, chromosomal, mitochondrial, or chloroplast DNA or ribosomal, transfer, heterogeneous nuclear, or messenger RNA. Additionally, methylated DNA and small interfering RNA (siRNA) and microRNA (miRNA) can be sequenced. RNA can be converted into more stable cDNA through the use of a reverse transcription enzyme (reverse transcriptase). Additionally, non-naturally occurring nucleic acids that are susceptible to enzymatic synthesis and degradation may be used in embodiments of the present invention.

Methods for preparing and isolating various forms of nucleic acids are known. See for example, Berger and Kimmel, eds., *Guide to Molecular Cloning Techniques*, Academic Press, New York, N.Y. (1987); and Sambrook, Fritsch and Maniatis, eds., *Molecular Cloning: A Laboratory Manual*, $2^{nd}$ ed., Cold Spring Harbor Press, Cold Spring Harbor, N.Y. (1989). Large strands of nucleic acids can be broken into smaller units for sequencing using shearing forces and restriction enzymes, for example. However, embodiments of the present invention are not limited to a particular method for the preparation of nucleic acids.

Methods are provided for sequencing nucleic acids in which amplification of the nucleic acid sample (i.e., increasing the number of copies of nucleic acid molecules in the sample) optionally does not have to occur. As much as one third of the error reported during the sequencing of a nucleic acid sample has been reported to be due to errors introduced during the bulk amplification of the nucleic acid sample. By not amplifying the sample to be sequenced, amplification-related errors can be avoided. Additionally, avoiding amplifying a sample avoids the concentration bias that can develop when a sample is amplified. The concentration bias that occurs during amplification is a result of the selective amplification advantage found for certain sequence populations, such that some sequences are amplified preferentially to a greater extent than other sequences. Because amplification-related errors are reduced, the methods of the present invention are useful for surveying for rare mutations among samples having a variety of components (mixed background components).

FIG. 1 depicts a generalized nucleic acid sequencing strategy according to embodiments of the invention. In FIG. 1, an array of detection regions 100, such as, for example, electronic sensors, having reaction and detection regions 110 and immobilized DNA molecules 120 is shown. One DNA molecule to be sequenced is immobilized per detection region 110 in this example, although more than one DNA molecule (that are copies of the same molecule) are optionally immobilized in the sensor region also. Optionally, the detection regions 110 are formed in depressions or wells in a substrate surface. In embodiments of the invention one DNA molecule is immobilized in the detection region 110. In other embodiments of the invention, a plurality of molecules are immobilized. Before sequencing a sample of DNA, overlapped DNA fragments are immobilized randomly on the surface of a substrate so that statistically one DNA molecule 120 occupies the reaction and detection region 110. A sample of DNA is optionally fragmented into smaller polymeric molecules using, for example, restriction enzymes or mechanical forces (shearing). The immobilized nucleic acid is primed with a primer 125 that is terminated with a nuclease resistant base and nucleic acid synthesis and deconstruction reactions are performed and amplified chemical products of the synthesis reactions 130 are created in the detection regions 110. The detection of reaction products indicates the identity of the next complementary nucleoside. The identified base position is then filled with a matching nuclease resistant blocking nucleoside polyphosphate, and the reaction is repeated to determine a matching base for the next available position on the DNA strand 120. These elements of the method (identification of a base position and filling the position with a nuclease resistant blocking version of the matching nucleotide that has been determined by the identification reaction) are repeated to determine sequence information for the surface-attached DNA strand 120. The number of times the reaction is repeated depends in part on the number of bases of DNA to be sequenced. In this example, the amplified chemical products 130 are detected electronically and sequence data for the immobilized DNA molecules are assembled. Amplified chemical products in a reaction and detection region 110, such as, for example, a gate of a FET, alter the current flow and capacitance between the source and the drain allowing electronic detection of the amplified products. Detected reaction products and their corresponding positions in the array are recorded and analyzed using a computer and analysis software. Data from regions having no immobilized nucleic acid sample or a plurality of immobilized samples are distinguished. Additionally, a computer is optionally used not only to direct the addressing and monitoring of the reaction regions of the array, but also to provide reagents to the array from fluidicly coupled resevoirs. In some embodiments the array is a chip comprising integrated electronics and or part of a microfluidic device or a microfluidic device coupled to a chip or computer having electronics that are capable of performing some or all of the features of addressibly monitoring reaction regions (recording signals from reaction regions) and addressibly supplying reagents to reaction regions. Additionally, a computer analyzes data and assembles sequence information.

Electronic sensors are monitored individually or as a group. The sensor array allows, for example, many immobilized DNA molecules to be sequenced simultaneously through the monitoring of individual reaction regions. The immobilized DNA molecules can either be a sample to be sequenced or capture DNA probes of known sequence can be first immobilized and then the sample to be sequenced can be hybridized to the immobilized probes. The capture probes have a sequence designed to hybridize to complementary sections of the sample DNA. Typically, DNA molecules to be immobilized are diluted so that statistically each sensor has one DNA molecule immobilized. Information from electronic sensors showing ambiguous results is disregarded. Sequence information is assembled from the sensors on a computer. Standard silicon and semiconductor processing methods allow a highly integrated sensor array to be made. For example, a 1 cm$^2$ silicon wafer chip can hold as many as 1×10$^8$ sensor regions having an area of about 1 μm$^2$.

In additional embodiments, multiple molecules of the same sequence are used in one sensor. The attachment of many DNA molecules having the same sequence in a sensor region is accomplished for example, by attaching a carrier containing many DNA molecules of the same sequence onto a sensor region, using, for example, emulsion polymerization techniques. Emulsion polymerization amplifies DNA molecules inside water bubbles surrounded by oil. The water bubbles contain a single primer-coated bead and a single initial DNA molecule that attaches to the bead and is amplified by enzymes in the water bubble. The bead becomes the carrier of an amplified sequence of DNA. The DNA molecule to be sequenced can also be amplified in situ after attachment to the sensor region. Additionally, the DNA molecule can be amplified using rolling circle amplification forming one long molecule having many repeats of the same sequence.

Figure 2:
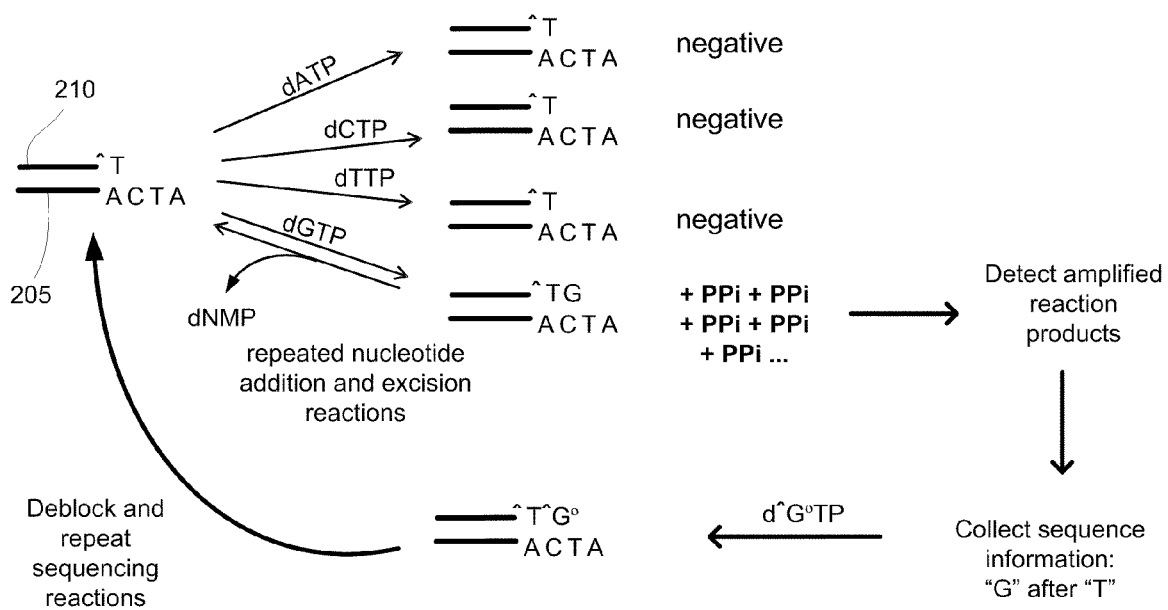
FIG. 2 outlines a general nucleic acid sequencing strategy using the chemical amplification of nucleic acid synthesis reaction products and the detection of amplified reaction products to assemble sequence information.

FIG. 2 diagrams a method for providing amplified chemical signals and sequencing data for nucleic acid sequencing reactions. In FIG. 2, a DNA molecule to be sequenced 205 is primed with a primer 210 that is terminated with an exonuclease resistant nucleotide which, in this example, is a thymine (nuclease resistance being indicated in FIG. 2 with a "^"). The chemical products resulting from the incorporation of a complementary dNTP (a deoxynucleotide triphosphate, e.g., dATP (deoxyadenosine triphosphate), dCTP (deoxycytidine triphosphate), dGTP (deoxyguanosine triphosphate), or dTTP (deoxythymidine triphosphate), for example) or dNTP analog, into a nucleic acid strand to be sequenced 205 are amplified through the repeated addition and excision of the next complementary nucleotide onto the priming sequence 210. In one embodiment, individual test reactions are performed using one of four dNTPs and a determination is made regarding the next complementary nucleotide in the nucleic acid to be sequenced. In general, a test reaction comprises a polymerase, an exonuclease, and a deoxynucleoside triphosphate (such as dATP, dCTP, dTTP, or dGTP), a nucleoside tetra- or pentaphosphate, or a labeled nucleoside analog (a labeled nucleoside tri-, tetra-, pentaphosphate, or oligophosphate). Labels include redox labels that are redoxigenic, such as aminopheny, hydroxyphenyl, or napthyl groups attached to a terminal phosphate of the nucleoside tri-, tetra-, pentaphosphate or oligophosphate that become redox active after the removal of phosphate groups. In general, a redoxigenic label is a label that becomes redox active after its removal from the polyphosphate nucleoside upon the incorporation of the labeled nucleoside into a nucleic acid molecule. The redoxigenic label undergoes further reaction after incorporation-related cleavage from the nucleoside polyphosphate, such as the removal of phosphate or pyrophosphate groups, before becoming redox active. After incorporation of the redox labeled nucleoside polyphosphate, phosphate groups are removed from the label using a phosphatase enzyme. The released redoxigenic label is detected electrochemically and or using redox cycling techniques.

In FIG. 2, a complementary nucleoside is incorporated into and excised from the growing DNA molecule (primer strand) 210 through the action of a polymerase enzyme. Typical useful polymerase enzymes include DNA polymerases, such as for example, E. coli DNA polymerase I and the commercially available 9 N and its modified derivatives such as, Therminator DNA polymerases (available from New England Biolabs, Inc., Ipswich, Mass.). Where there is a cytosine, for example, on the strand to be sequenced 205, a guanine will be incorporated, where there is a thymine, an adenosine will be incorporated, and vice versa. If the nucleoside triphosphate is incorporated into the growing strand 210 in the test reaction, then a pyrophosphate ion (i.e., a pyrophosphate, PPi, or $P_2O_7^{-4}$), polyphosphate, or labeled poly- or pyrophosphate is released. In an amplification reaction, an exonuclease is used to remove the incorporated nucleoside monophosphate (dNMP$^{-2}$), allowing another complementary nucleoside triphosphate to be incorporated and additional PPi to be released. Repetition of these addition and excision reactions provides amplification of the reaction products of nucleic acid synthesis. Thus, a positive test reaction (i.e., the detection of chemically amplified products) indicates that the base on the template DNA strand to be sequenced 210 immediately after the priming base (the 3' base) of the primer strand 210 is complementary to the test base (the one of four dNTPs that was used in the synthesis and deconstruction reaction). These elements of addition and excision are repeated at least until a detectable signal is realized. Optionally, the reaction sequence can be terminated when a positive result is obtained indicating the incorporation of a dN'TP, without testing the remaining bases for incorporation (complementarity).

In FIG. 2, to sequence the next base on the template, the first identified base on the primer strand 210 is filled or replaced with an identified nuclease-resistant blocking nucleotide (3' blocking is indicated with a "o" in FIG. 2) that then becomes the priming base for the next test reaction after deblocking. In general, blocking nucleotides prevent further nucleic acid synthesis by reversibly blocking the addition of a nucleic acid to the end of the nucleic acid molecule. Nuclease-resistant blocking nucleosides are, for example, ribonucleosides or other modified nucleosides and are described more fully herein. A variety of polymerases are available that can incorporate ribonucleotides or modified nucleosides into DNA, such as for example, the commercially available Therminator DNA polymerase (available from New England Biolabs, Inc., Ipswitch, Mass.). See also, for example, DeLucia, A. M., Grindley, N. D. F., Joyce, C. M., *Nucleic Acids Research*, 31:14, 4129-4137 (2003); and Gao, G., Orlova, M., Georgiadis, M. M., Hendrickson, W. A., Goff, S. P., *Proceedings of the National Academy of Sciences*, 94, 407-411 (1997). Exemplary nuclease resistant bases include alpha-phosphorothioate nucleosides having different chiralities, and exemplary nucleases that cannot digest the specific chiral isomer of the phosphorothioate bond include polymerase associated exonuclease such as the exonuclease activity of T4 or T7 Polymerase (which can not digest S-chiral conformation of the phosphorothioate bond). Some polymerase enzymes possess intrinsic exonuclease activity therefore it is not always necessary to use two different enzymes for the addition and excision reactions. Reactions in which no significant amount of product is detected indicate that the test reaction provided a nucleotide that was not complementary to the next base of the nucleic acid to be sequenced. After addition of the next known complementary nucleotide to the primer 210, the primer 210 is deblocked through removal of the 3' blocking group and the identity of the next complementary nucleotide is determined by repeating the test reactions as described above.

Figure 3A:
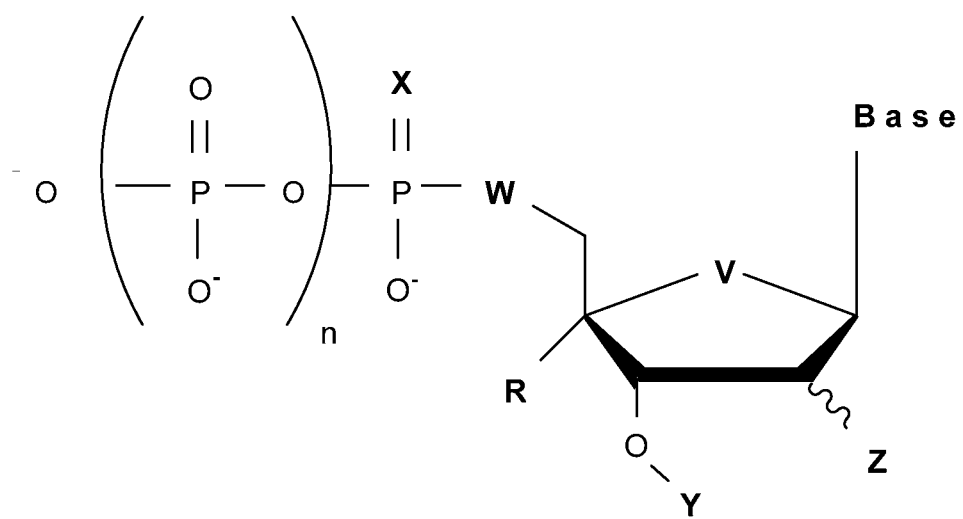
FIGS. 3A and 3B provide exemplary nuclease resistant blocking nucleosides.
Figure 3B:
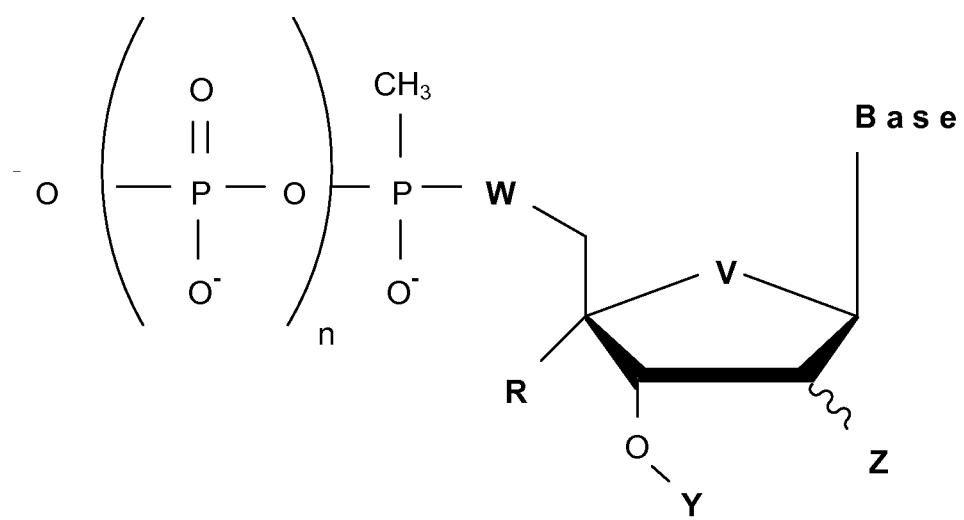

FIGS. 3A and 3B provide structural representations of exemplary nuclease resistant blocking nucleotides. In FIG. 3A, the base, B, is adenine (A), cytosine (C), guanine (G), thymine (T), uracil (U), or an analog thereof, such as, for example, a modified base, a hydrophobic base analog, such as for example, 2,4-difluoro-5-toluene (Kool E. T., *Acc. Chem. Res.*, 35, 936-943 (2002)), universal base (3-nitropyrrole or 5-nitroindole) or isoguanine and isocytosine; n is a number between and including 2 and 4, X is S, —BH, Se, or O; Y is azidomethyl, allyl, acetyl, or o-nitrobenzyl; Z is H, OH, F, SH, $N_3$, OMe, or $NH_2$; R is a group conveying nuclease resistance such as, for example, $N_3$, $NH_2$, $CH_3(CH_2)_mNH$ where m is a number between and including 0 and 9, benzylamino, AcO, MeO, hydroxymethyl, and benzyloxymethyl or a locked DNA base (i.e., nucleoside analogs having a $CH_2$—O bridge between the 2' and 4' position of the sugar ring. Because of the bridge, the sugar ring conformation is considered locked.), or R is H; W is O, S, $CH_2$, $CF_2$, CHF, or NH; and V is O, S, Se, $CH_2$, $CF_2$, CHF, or NH. In FIG. 3B, the base, B, is adenine (A), cytosine (C), guanine (G), thymine (T), uracil (U), or an analog thereof, such as, for example, a modified base, a hydrophobic base analog, such as for example, 2,4-difluoro-5-toluene (Kool E. T., *Acc. Chem. Res.*, 35, 936-943 (2002)), universal base (3-nitropyrrole or 5-nitroindole) or isoguanine and isocytosine; n is a number between and including 2 and 4; Y is azidomethyl, allyl, acetyl, or o-nitrobenzyl; Z is H, OH, F, SH, $N_3$, OMe, or $NH_2$; R is a group conveying nuclease resistance such as, for example, $N_3$, $NH_7$, $CH_3(CH_2)_mNH$ where m is a number between and including 0 and 9, benzylamino, AcO, MeO, hydroxymethyl, and benzyloxymethyl or a locked DNA base (i.e., nucleoside analogs having a $CH_2$—O bridge between the 2' and 4' position of the sugar ring. Because of the bridge, the sugar ring conformation is considered locked.), or R is H; W is O, S, $CH_2$, $CF_2$, CHF, or NH; and V is O, S, Se, $CH_2$, $CF_2$, CHF, or NH. Since modifications to X, W, V, and R of the nucleoside confer nuclease resistance, at least one of the following is the case: 1) X, W, and or V is/are not O, or 2) R is not H. In general, when X is a sulfur atom, a selenium atom, a —$CH_3$ group (FIG. 3B), or a —BH group (an alpha-thiotriphosphate, alpha-methyltriphosphate, alpha-boranophosphate), when W is $CH_2$, $CF_2$, CFH, or S, when V is S, $CH_2$, $CF_2$, or CFH, and or when R is a(n) $N_3$, $NH_2$, $CH_3(CH_2)_mNH$ where m is a number between and including 0 and 9, benzylamino, AcO, MeO, hydroxymethyl, and benzyloxymethyl or a locked DNA base, the nucleotide has polymerase resistant properties. When Y is azidomethyl, allyl, or o-nitrobenzyl, the nucleotide has blocking properties. In some embodiments, nuclease resistant blocking nucleotides have one functional group that confers nuclease resistance and one functional group that confers blocking properties. Alternatively, the nuclease resistant blocking nucleotide has two functional groups that confer nuclease resistance and one functional group that confers blocking properties. Further alternatively, the nuclease resistant blocking nucleotide has three functional groups that confer nuclease resistance and one functional group that confers blocking properties. Optionally, the nucleotide of FIGS. 3A and 3B is provided as an acid or a neutral salt that is compatible with nucleic acid synthesis reactions, such as for example, as a $H^+$, $Na^+$, $K^+$, triethylamine, or tributlyamine.

Reversible terminators that have been modified at the 3' position with, for example, 3'-azidomethyl or 3'-allyl, are cleaved chemically to deblock the nucleotide, using for example, TCEP (tricarboxylethylphosphine) for 3'-azidomethyl and aqueous Pd-based catalyst to remove 3'-allyl group, and 3' o-nitrobenzyl blocking groups are cleaved photochemically.)

Figure 4:
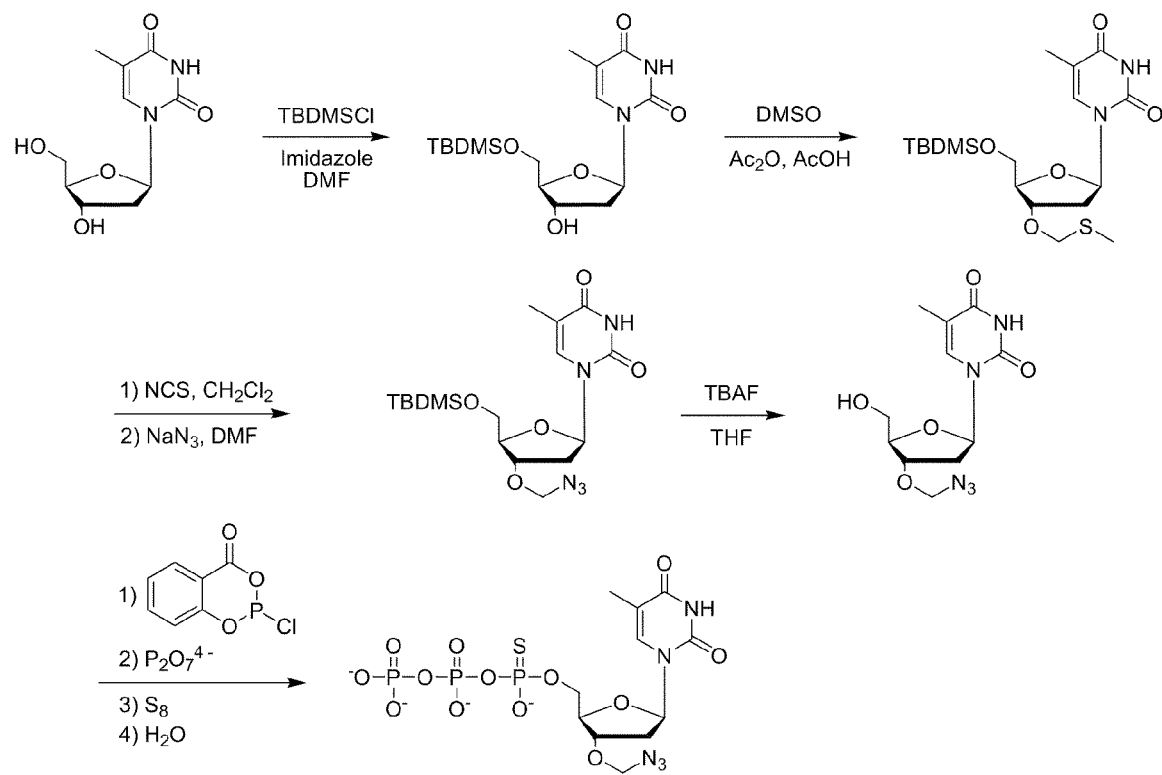
FIG. 4 demonstrates a synthesis scheme for a nuclease resistant blocking nucleoside.

FIG. 4 provides an exemplary synthesis scheme for an exemplary bifunctional (blocking and nuclease resistant) nucleotide, 3'-azidomethyl dTTPαS. In FIG. 4, the synthesis of 3'-azidomethyl thymidine is found in, for example: Guo et al., *PNAS*, 105(27), 9145-9150 (2008). The conversion of 3'-azidomethyl thymidine was carried out by adapting Eckstein chemistry for synthesis of thiotriphosphate: Ludwig and Eckstein, *J. Org. Chem.*, 54, 631-635 (1989).

Figure 5:
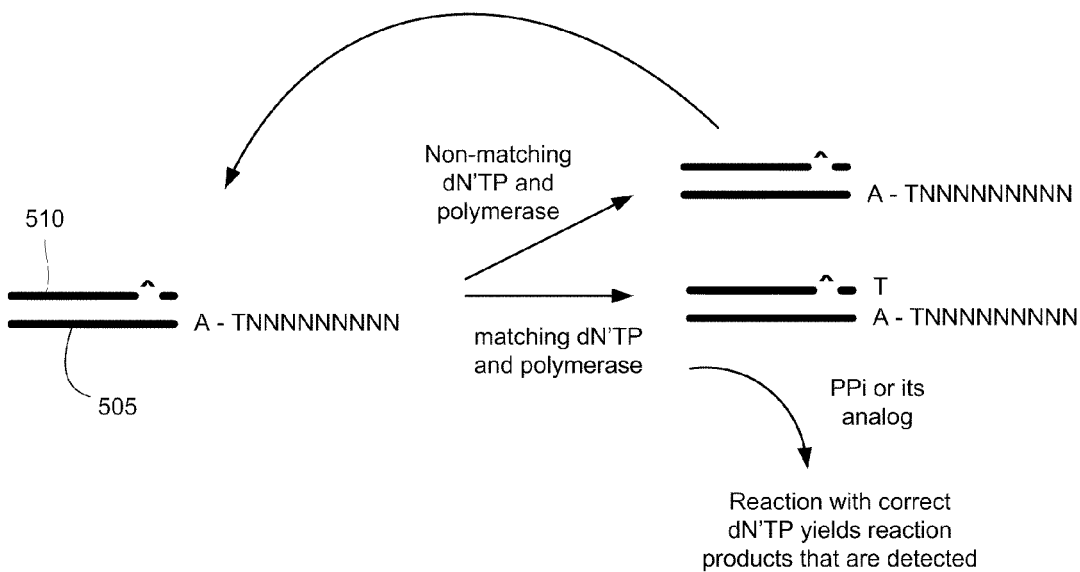
FIG. 5 outlines additional nucleic acid sequencing reactions.
Figure 5:
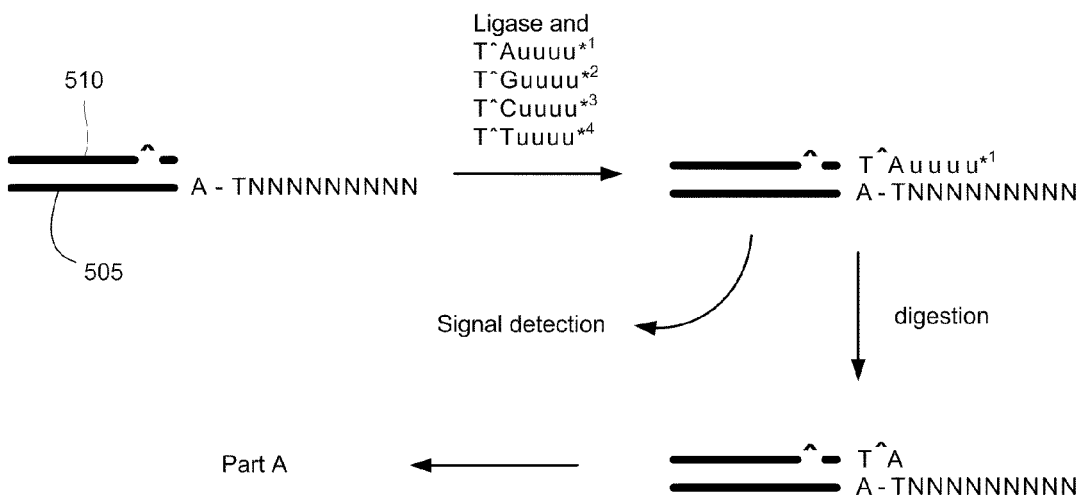

FIG. 5 provides an additional scheme that is useful for sequencing nucleic acids. In FIG. 5, Parts A and B, a nucleic acid to be sequenced 505 (in which "NNNNNNNNN" generically indicates nucleosides of the nucleic acid to be sequenced 505) is primed with a nuclease resistant oligonucleotide 510 (nuclease resistance being indicated by a "^" in FIG. 5) and sequencing reactions are performed. In Part A of FIG. 5, the chemical products resulting from the incorporation of a dN'TP (a deoxynucleoside triphosphate or its analog) complementary to the first unhybridized base of the nucleic acid strand to be sequenced 505 are amplified through the repeated addition and excision of the next complementary nucleoside onto the priming sequence 510. Analogs of nucleotides include, for example, terminal phosphate labeled analogs, polyphosphate analogs having 4 to 5 phosphate groups, and labeled polyphosphate analogs having 4 to 5 phosphate groups. Labels for the terminal phosphate include redox labels that can be detected electrochemically, such as, for example, redoxigenic labels that can be detected through redox cycling techniques. Redox labels are also detected through other types of electrochemical analysis, such as cyclic voltammetry (CV) or swiping wave voltammetry (SWV). In general, redoxigenic lables are reox inactive species that become redox active when cleaved from the phosphate group to which they are attached. Cleavage is accomplished, for example through the use of a phosphatase enzyme. In one embodiment, individual test reactions are performed using one of four dN'TPs and a determination is made regarding the next complementary nucleotide in the nucleic acid to be sequenced. In general, a test reaction comprises a polymerase, an exonuclease, and a deoxynucleoside triphosphate or nucleotide analog (such as dA'TP, dC'TP, dT'TP, or dG'TP). A complementary nucleotide (or nucleotide analog) is incorporated into the growing DNA molecule 510 that is terminated with a nuclease resistant base through the action of a polymerase enzyme. The newly added nucleotide is then removed through the action of an exonuclease and another complementary nucleotide (or nucleotide analog) is added. These elements of addition and excision are repeated at least until a detectable signal is realized. Optionally, the reaction sequence can be terminated when a positive result is obtained indicating the incorporation of a dN'TP, without testing the remaining bases for incorporation (complementarity).

After the identity of the next complementary base has been determined (Part A, FIG. 5), a set of non-natural oligonucleotides is applied to the primer 510—molecule to be sequenced 505 hybrid under conditions that allow a complementary oligonucleotide to selectively hybridize the molecule to be sequenced 505 in the presence of ligase enzyme (Part B, FIG. 5). In Part B, the set of non-natural oligonucleotides is made up of oligonucleotides containing the next complementary nucleoside as determined in Part A (which in this example is a T), one of the four polyphosphate nucleosides (A, C, G, or T) that has nuclease resistance (nuclease resistance being indicated by a "^" in FIG. 5) (each of the oligonucleotides in the set having a different one of the four nucleosides in the 3' position next to the known base), four universal nucleosides, and a label attached to one of the universal nucleosides. In some embodiments, the label is attached to a terminal universal nucleoside. Alternately, the oligonuceotides comprise an additional thymidine to which a label is attached. After selective hybridization, the ligase enzyme ligates the complementary oligonucleotide to the primer strand 510.

In general, a universal base (or nucleoside) is a nucleobase analog that is capable of hybridizing non-selectively to each of the natural bases. The universal nucleoside analogs are capable of pairing with each natural base. In FIG. 5, each of the four different non-natural oligonucleotides bears a different detectable label, that indicates the identity of the second nucleotide next to the next complementary oligonucleotide (e.g., whether the second nucleotide is an A, a C, a G, or a T). In this embodiment, the oligonucleotides comprise four universal nucleotides, however, other numbers of universal nucleotides are possible, such as for example, 4 to 7 universal nucleotides. Some exemplary useful universal nucleotides include 3-nitropyrrole or 5-nitroindole, and universal nucleotides bearing labels that can be used to make labeled non-natural oligonucleotides include, for example, modified 5-nitroindole with a label attached to a linker at the 3-position. In general, a label provides a detectable signal, and can be, for example, a fluorescent label. Typical useful ligase enzymes include T4 DNA ligase, *E. coli* ligase, or thermostable ligases (available, e.g., from New England Biolabs, Ipswich, Mass.). After ligation, the solution containing the set of non-natural oligonucleotides is removed, and the label from the ligated non-natural oligonucleotide is detected. Through the detection of the label, the identity of the second complementary nucleotide is determined. In FIG. 5, part B, for example, if label 1 is detected, then the next complementary nucleoside base is an A, and the base on the nucleic acid to be sequenced 505 is a T. The universal nucleotides are then digested away leaving a nuclease resistant primer strand 510 that has been lengthened by two complementary nucletotides and the test reactions of Part A and B are repeated to determine the identity of the third and fourth complementary nucleosides. In general, Parts A and B are repeated as many times as necessary, necessity being dictated by the number of unknown nucleotides for which the identity is to be determined on the molecule to be sequenced 505.

Figure 6:
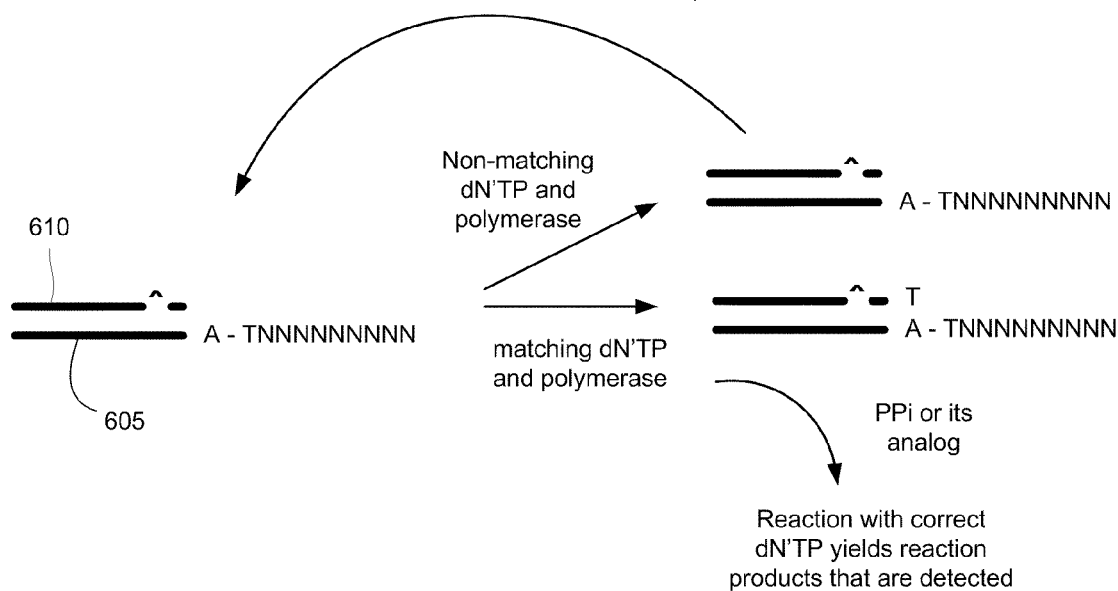
FIG. 6 provides additional nucleic acid sequencing reactions.
Figure 6:
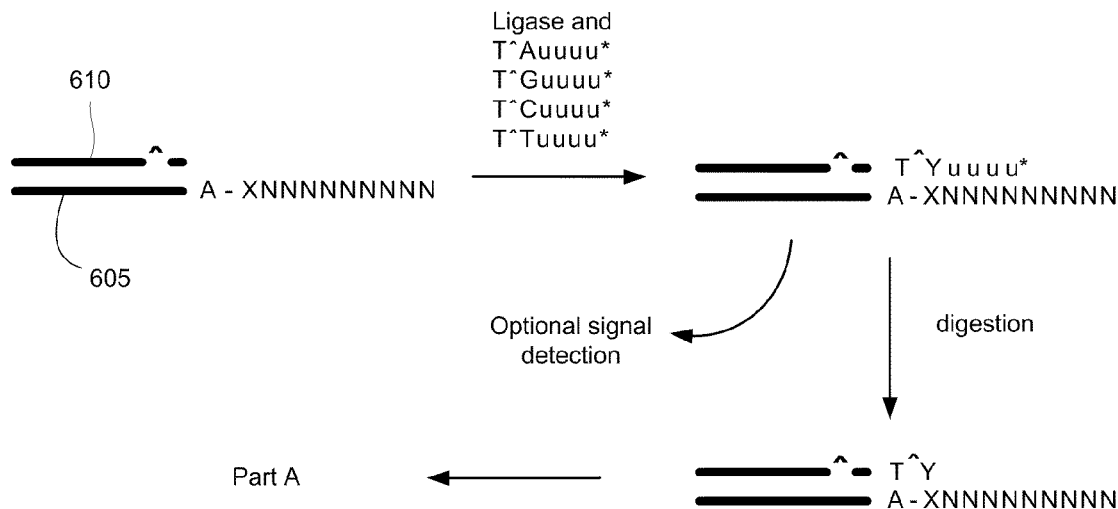

FIG. 6 provides an additional nucleic acid sequencing scheme that employs a non-natural oligonucleotide. In FIG. 6, Parts A and B, a nucleic acid to be sequenced 605 (in which "NNNNNNNNN" generically indicates nucleosides of the nucleic acid to be sequenced 605) is primed with a nuclease resistant oligonucleotide 610 (nuclease resistance being indicated by a "^" in FIG. 6) and sequencing reactions are performed. In Part A of FIG. 6, the chemical products resulting from the incorporation of a dN'TP (a deoxynucleotide or its analog) complementary to the first unhybridized base of the nucleic acid strand to be sequenced 605 are amplified through the repeated addition and excision of the next complementary nucleotide (or its analog) onto the priming sequence 610. Analogs of nucleic acids include, for example, terminal phosphate labeled analogs, polyphosphate analogs having 4 to 5 phosphate groups, and terminal phosphate labeled polyphoshate analogs having 4 to 5 phosphate groups. Labels for the terminal phosphate include redox labels that can be detected electrochemically, such as, for example, redoxigenic labels that can be detected through redox cycling (or other electrochemical detection) techniques. In one embodiment, individual test reactions are performed using one of four dN'TPs and a determination is made regarding the next complementary nucleotide in the nucleic acid to be sequenced. In general, a test reaction comprises a polymerase, an exonuclease, and a deoxynucleoside triphosphatase (such as dA'TP, dC'TP, dT'TP, or dG'TP). A complementary nucleotide is incorporated into the growing DNA molecule 610 through the action of a polymerase enzyme and excised through the action of a exonuclease enzyme. Addition and excision are repeated to build up the concentration of nucleic acid synthesis products. Optionally, the reaction sequence can be terminated when a positive result is obtained indicating the incorporation of a dN'TP, without testing the remaining bases for incorporation (complementarity).

After the identity of the next complementary base has been determined (Part A, FIG. 6), a set of oligonucleotides is applied to the primer 610—molecule to be sequenced 605 hybrid under conditions that allow a complementary oligonucleotide to hybridize the molecule to be sequenced 605 in the presence of ligase enzyme (Part B, FIG. 6). In Part B, the set of oligonucleotides is made up of oligonucleotides containing the next complementary nucleotide as determined in Part A, one of the four nucleotides (A, C, G, or T) that has nuclease resistance (nuclease resistance being indicated by a "^" in FIG. 6), four universal nucleotides, and optionally, a label attached to one of the universal nucleotides. In this embodiment, the non-natural oligonucleotides comprise four universal nucleotides, however, other numbers of universal nucleotides are possible, such as for example 4 to 7 universal nucleotides. Some exemplary useful universal nucleotides include 3-nitropyrrole or 5-nitroindole. In general, a label provides a detectable signal, and can be, for example, a fluorescent label. Typical useful ligase enzymes include T4 DNA ligase, *E. coli* ligase or thermostable ligases. The label is optionally detected after the removal of the non-natural non-hybridized oligonucleotides, indicating the successful hybridization of a non-natural oligonucleotide to the nucleic acid to be sequenced 605. The universal nucleotides are then digested away leaving a nuclease resistant primer strand 610 that has been lengthened by two complementary nucletotides. The test reaction of Part A is repeated to determine the identity of the third complementary nucleotide. In general, Parts A and B are repeated as many times as necessary, necessity being dictated by the number of unknown nucleotides for which the identity is to be determined on the molecule to be sequenced 605. In this embodiment, only every other base is sequenced, since in FIG. 6, Part B, a mixture of oligonucleotides for the second base position is provided (i.e., the identities of X and Y are unknown in this embodiment). In order to determine the sequence of the entire nucleic acid to be sequenced, the reactions are repeated using a primer that is n base(s) longer or shorter that the primer strand used in the first instance, where n is an odd number between and including 1 and 5. Typically, n is one.

Figure 7:
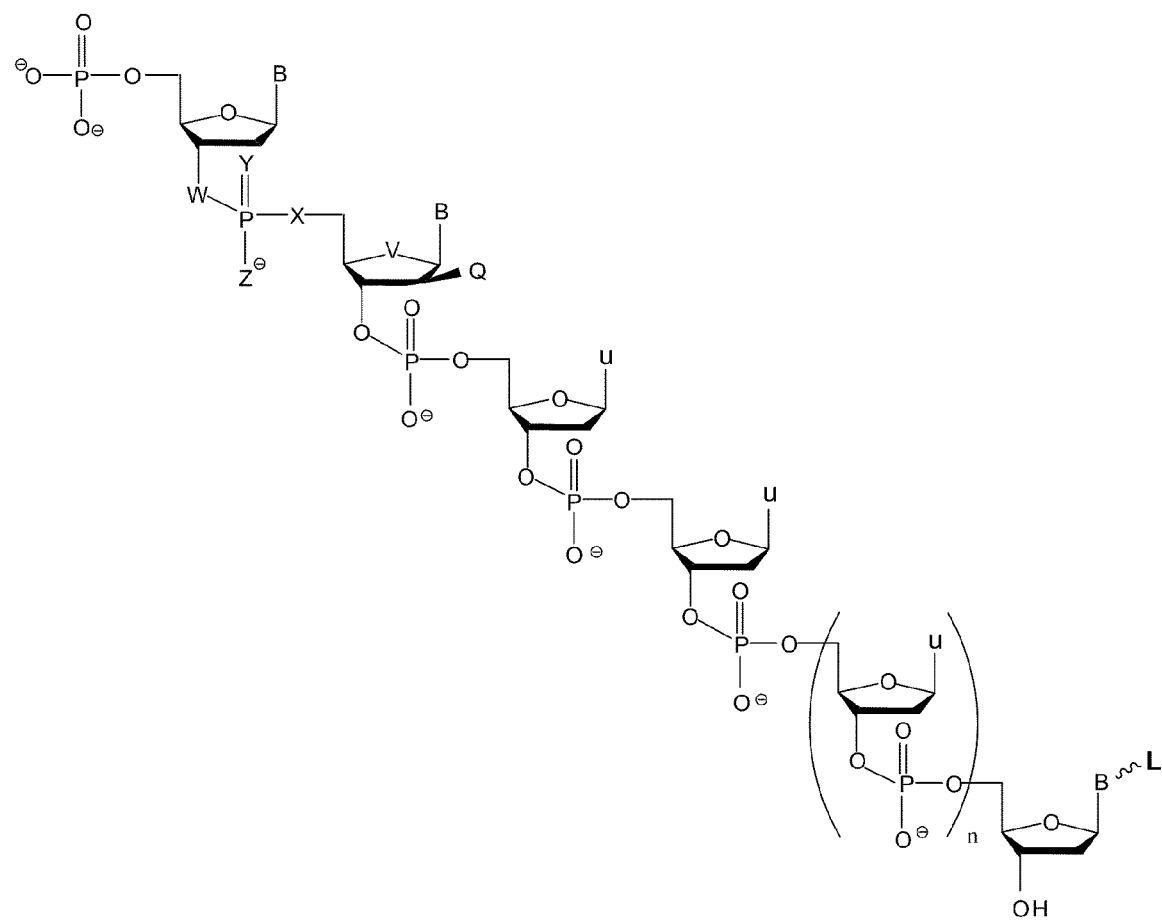
FIG. 7 shows a non-natural oligonucleoside useful in nucleic acid sequencing reactions.

FIG. 7 provides exemplary non-natural oligonucleotides useful in embodiments of the invention. In FIG. 7, B is a nucleic acid base (such as A, G, C, or T) or a nucleobase analog, u is a universal base (such as, for example, 5-nitroindole, 3-nitropyrrole), X is O, S, NH, $CH_2$, $CF_2$, CFH, or Se, Y is O, S, Se, B, or —OMe; Z is O, S, Se, —$CH_3$, carboxyl, or carboxylethyl; W is NH, O, S, $CH_2$, $CF_2$, CFH, or Se; V is O, S, or Se; Q is F, Cl, Br, or H; L is a label, such as, for example, a fluorescent or redox label, and n is a number between and including 2 and 5. In general, one modification confers nuclease resistance, however combinations of modifications improve nuclease resistance. Therefore, in the non-natural oligonucleotide, at least one of the following is the case: 1) X, Y, Z, W, or V is not O or 2) Q is not H. Analogs of nucleic acid bases include isoguanine and isocytosine, which have their amine and ketone inverted compared to natural guanine and cytosine. As mentioned herein, in general, a universal base (or nucleotide) is a nucleobase analog that is capable of hybridizing non-selectively to each of the natural bases. Typically, the label is located, as shown in FIG. 7, on the 3' end of the oligonucleotide. In one embodiment, the second base from the 5' end of the oligonucleotide shown in FIG. 7 is 2'-F-arabinonucleic acid (FANA). Further, in an embodiment, the label is a fluorescent label. Exemplary fluorescent labels include fluorescein, TAMRA, R6G, Cy3, Cy5, and coumarin, although many other examples are commercially available. Exemplary redox labels include ferrocene, 4-hydroxyphenol, 4-aminophenol, or 1,4-napthyldiol, AATO MB2 (a derivative of the redox dye Methylene Blue that has a carboxylic acid functional group for coupling to biomolecules).

Figure 8:
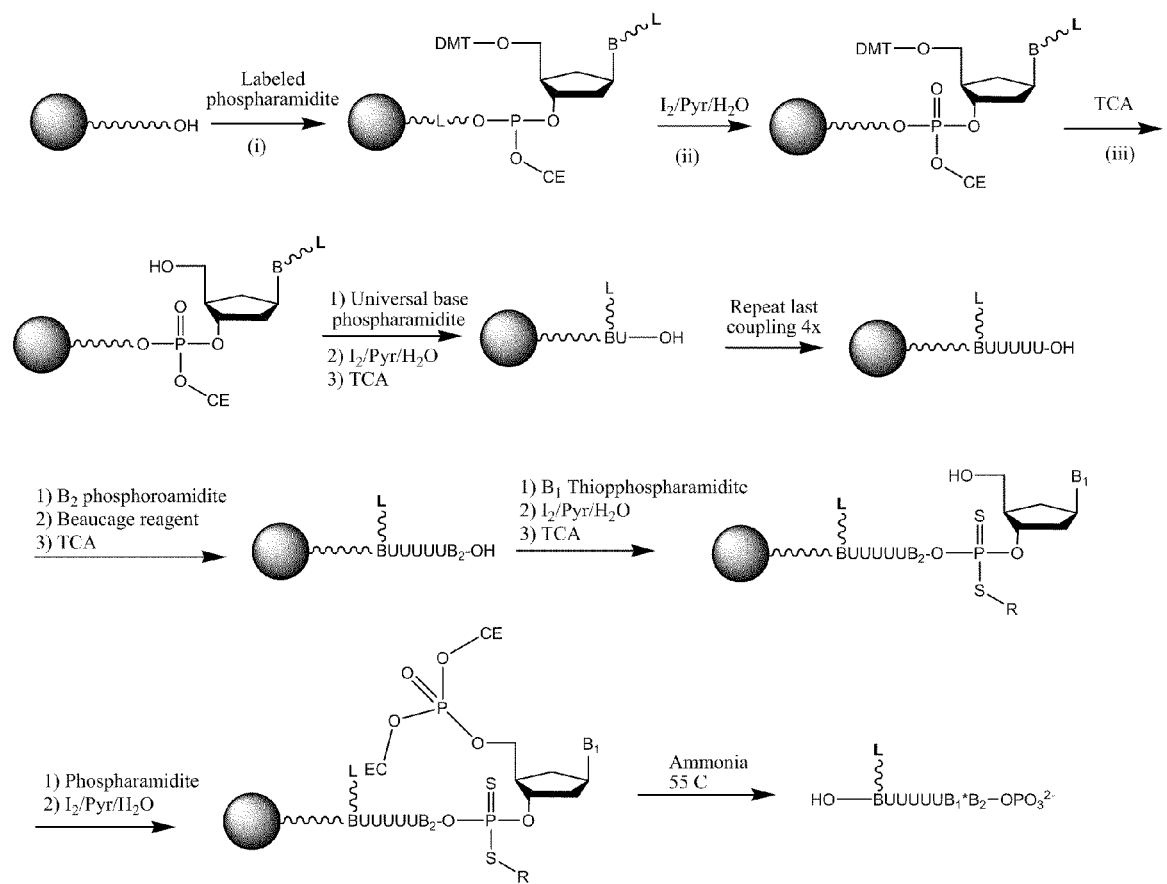
FIG. 8 is an exemplary synthetic scheme for a non-natural oligonucleoside useful in nucleic acid sequencing reactions.

FIG. 8 demonstrates a synthetic scheme for making a non-natural oligonucleotide that contains a phosphorodithioate linkage. The reactions are optionally performed using solid-phase synthesis techniques. In general, the reactants shown in FIG. 8 are commercially available from Glen Research (Sterling, Va.). In FIG. 8 standard conditions are used. However, in the synthesis of phosphorodithioate, thiophospharamidite and Beaucage reagent are used. Both of these two reagents are also available from Glen Research. The cleavage and deprotection are done under mild conditions due to the presence of phosphorodithioate and can be carried out at room temperature overnight.

Typical useful polymerase enzymes include DNA polymerases with or without 3' to 5' exonuclease activities, such as for example, *E. coli* DNA polymerase I, Klenow fragment of *E. Coli* DNA polymerase I, phusion DNA polymerase, Therminator DNA polymerase, reverse transcriptase, Taq DNA polymerase, Vent DNA polymerase (all available from New England Biolabs, Inc., Ipswitch, Mass.), T4 and T7 DNA polymerases, and Sequenase (all available from USB, Cleveland, Ohio). A variety of polymerases are available that can incorporate ribonucleotides or modified nucleotides into DNA, such as for example, the commercially available Therminator DNA polymerase (available from New England Biolabs, Inc., Ipswitch, Mass.) or genetically engineered DNA polymerases. See also, for example, DeLucia, A. M., Grindley, N. D. F., Joyce, C. M., *Nucleic Acids Research*, 31:14, 4129-4137 (2003); and Gao, G., Orlova, M., Georgiadis, M. M., Hendrickson, W. A., Goff, S. P., *Proceedings of the National Academy of Sciences*, 94, 407-411 (1997). Exemplary nuclease resistant nucleotides that can be incorporated into growing DNA strands but that are resistant to digestion by exonucleases (such as the 3' to 5' exonuclease active DNA polymerases or exonuclease I and III) include alpha-phosphorothioate nucleotides (available from Trilink Biotechnologies, Inc., San Diego, Calif.). Additionally, ribonucleotides can be incorporated into a growing DNA strand by Therminator DNA polymerase or other genetically engineered or mutated polymerases. Phi-29 DNA polymerase (available from New England Biolabs, Inc.) provides strand displacement activity and terminal deoxynucleotide transferase provides template independent 3' terminal base addition. In one embodiment exonuclease free polymerase is used in combination with Exo III exonulease.

Figure 9:
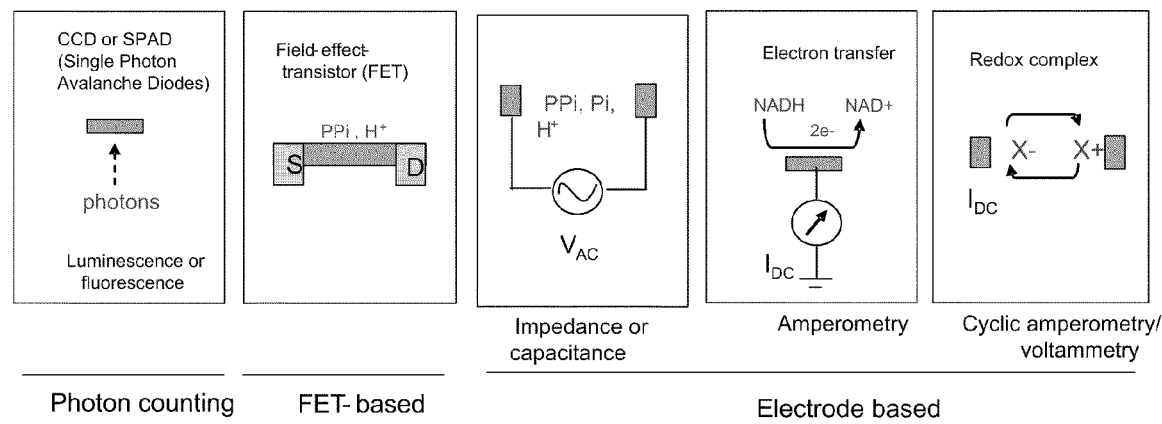
FIG. 9 shows exemplary sensing schemes that can be used to sequence nucleic acids using chemical amplification of signals.

FIG. 9 shows exemplary devices that are useful for detecting reaction products of nucleic acid synthesis and ligation reactions and performing nucleic acid sequencing according to embodiments of the invention. Possible sensing schemes include ones that measure or otherwise provide a response based on the primary reaction product content, such as for example PPi, Pi, $H^+$, and polymerized nucleotides. In the alternative, sensing schemes can detect the presence of labels (such as fluorescent or redox labels) and or the products of additional chemical reactions, such as for example, detecting the presence of photons, electron carriers, and or redox centers. Sensors include ones capable of photon counting, FET-based sensors, and electrode-based sensors that measure impedance or capacitance or that perform amperometry, cyclic amperometry, and or voltammerty. Discussions of the measurement of impedance or capacitance changes for biological molecules and reactions can be found, for example, in Daniels, J, Pourmand, N., *Electroanalysis*, 19:1239 (2007) and Daniels, J., Anderson, E., Lee, T., Pourmand, N., "Simultaneous Measurement of Nonlinearity and Electrochemical Impedance for Protein Sensing Using Two-tone Excitation," *Engineering in Medicine and Biology Society*, 30$^{th}$ International Conference of the IEE (2008). Micro and nanoelectrode arrays can be fabricated for electrode-based sensors. Electrodes can be fabricated as, for example, printed circuit boards. PPi is a product of nucleotide incorporation by DNA polymerase that can be enzymatically converted to NADH in a set of cascade reactions (see, for example, *Analytical Biochemistry*, 142(2):369-372 (1984)). NADH is an electron carrier that donates 2 electrons upon oxidation and is electrochemically detectable through the detection of the redox reaction. Polyphosphate can be converted into PPi through enzymatic reaction.

Further, for the detection of a redox label or species, the device can be a redox cycling sensor, such as, for example, those described in "Nanogap Chemical and Biochemical Sensors," U.S. patent application Ser. No. 12/655,578, filed Dec. 31, 2009, U.S. Pat. No. 8,500,979. In general, redox cycling is an electrochemical method in which a molecule that can be reversibly oxidized and or reduced (i.e., a redox active molecule) moves between at least two electrodes that are biased independently, one below a reduction potential and the other one above an oxidation potential for the redox active molecule being detected, shuttling electrons between the independently biased electrodes (i.e., the molecule is oxidized at a first electrode and then diffuses to a second electrode where it is reduced (or vice versa, it is first reduced and then oxidized, depending on the molecule and the potentials at which the electrodes are biased)). In redox cycling, the same molecule contributes a plurality of electrons to the recorded current resulting in the net amplification of the signal. In redox cycling applications, the space between the electrodes is on the nanometer scale. Redox-active molecules diffuse in the cavity between the two electrodes and shuttle multiple electrons between the electrodes, leading to amplification of the measured electrochemical current. Signals from the redox active species are potentially amplified greater than 100 times, depending on factors, such as the stability of the redox species and the diffusion of the redox species out of the sensing region. Electronic sensors are reliably fabricated in a CMOS (complementary metal oxide semiconductor) compatible manner allowing dense integration of sensor units (and optionally driving electronics) onto a single platform, such as for example a chip or silicon wafer typically used in integrated circuit manufacturing applications.

During a sequencing reaction involving nucleotide incorporation, charged phosphates, polyphosphates, or phosphate-containing complexes and protons are generated. These compounds can affect the potential or current flow of a sensor surface. When a sensor surface is coated with an affinity agent, such as a PPi or phosphate chelator (see, for example, "Solid Phase Chelators and Electronic Biosensors" U.S. patent application Ser. No. 12/655,459, filed Dec. 30, 2009.), the surface potential or charge distribution will be affected due to binding of the charged species on the surface of the sensor. In this case, FET devices are used as sensor. When an affinity agent is not used, transient changes in potential or current can also take place due to difference in diffusion rates of the positively charge protons and the negatively charged phosphate compounds, the transient imbalance of local charge distribution can cause either a potential difference or a current flow difference, that can be sensed by either voltage-based or current-based sensing methods. In this embodiment, the sensor surface is a metal (such as, for example, that of an extended gate FET device). When the metal sensor surface is exposed to an aqueous solution, depending on solution pH and the metal sensor's surface modification(s), the surface is likely to be rich either in positively charged or negatively species. When the sensor surface is rich in negatively charged species, it will attract protons generated in a nucleotide incorporation reaction. When the sensor surface is rich in positively charged species, the surface will attract more negatively charged phosphate compounds. These transient or constant surface interactions can also affect the surface potential and can be detected by voltage-based sensing methods or current-based sensing methods or a combination of methods, such as impedance-based sensing methods. In general, a sensor device has a sensing surface comprising metal with a metal interconnect that is functionally linked to a semiconductor sensing circuit. The sensing circuit is functionally connected to a semicoductor control circuit for sensor address, signal processing, signal input/output and power. A circuit is set of integrated electronic elements designed for desired functions. Different circuits or multiple circuits can be fabricated on the same support substrate such as a silicon wafter.

Figure 10:
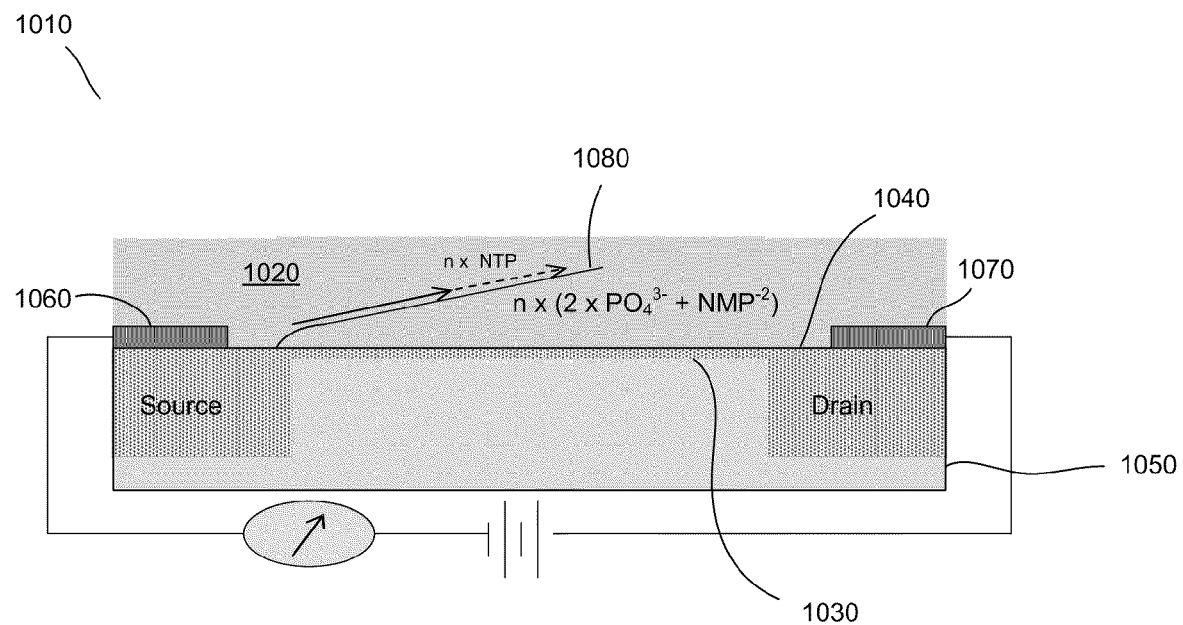
FIG. 10 is a schematic of device employing a field effect transistor that can be used for analyzing a solution-based nucleic acid sequencing reaction.

FIG. 10 shows a FET type sensor that is used for sensing a change in reactant or product concentrations resulting from DNA synthesis reactions, such as, for example, a change in PPi concentration. In sensor device 1010, the amplified chemical signals from nucleic acid synthesis reactions are converted into an electronic signal by an electronic sensing region 1030. For example, the sensor can be a P-type FET, an N-type FET, or a carbon nanotube transistor. See, for example, Janicki, M., Daniel, M., Szermer, M., Napieralski, A., *Microelectronics Journal,* 35, 831-840 (2004) and Rolka, D., Poghossian, A., Schoning, M., *Sensors,* 4, 84-94 (2004). In one embodiment, each sensor has a nano-sized reaction region 1020 (the gate) and a semiconductor transistor (channel) 1030 that are separated by an insulating layer 1040. The insulating layer 1040 is, for example, made from silicon oxide, silicon nitride, aluminum nitride, and or silicon oxynitride. The channel 1030 of the semiconductor transistor is comprised of, for example, a P- or N-type semiconductor, such as for example, silicon or germanium doped with boron, arsenic, phosphorous, or antimony. A solution in the reaction region 1020 forms a gate and the components of the sensor 1010 are typically placed on a substrate 1050. The source electrode 1060 and the drain electrode 1070 are typically comprised of conducting materials, such as for example, gold, copper, silver, platinum, nickel, iron, tungsten, aluminum, or titanium. The substrate 1050 is comprised of, for example, silicon, silica, quartz, germanium, or polysilicon. In further embodiments, the reaction region 1020 has dimensions of less than about 100 nm, less than about 1 µm, or less than about 10 µm. The reaction region can have dimensions in the range of 10 nm to 10 µm. The reaction region 1020 is used as part of the gate of the transistor. DNA 1080 is immobilized through attachment to a sensor surface by standard methods. For example, acrydite-modified DNA fragments can be attached to a surface modified with thiol groups and amine-modified DNA fragments can be attached to epoxy or aldehyde modified surfaces. In operation, variations in the potential between the solution (the gate) in the reaction region 1020 and the insulator 1040 surface modify the charge distribution in the channel 1030. Changes in the solution, such as changes in charge distribution created by the linearly amplified PPi molecules or bound charges associate with the DNA molecules, can be measured by changes in the conductivity or changes in the capacitance across the channel 1030. The sensor 1010 is optionally one of a plurality of sensors that forms an array of sensors.

Alternatively, extended gate FET sensor is used. An extended gate is a metal that is functionally connected to a FET device that is made by, for example, CMOS process. The metal of the extended gate has a surface area that is functionally connected to a region where a biochemical (sequencing) reaction takes place. The metal extended gate can be built in a process similar to the process used to build the interconnects on top of silicon substrate where FET sensors are located. The exposed surface of the extended gate is made of electrochemically stable noble metals, such as, Au, Pt, or Pd.

Figure 11:
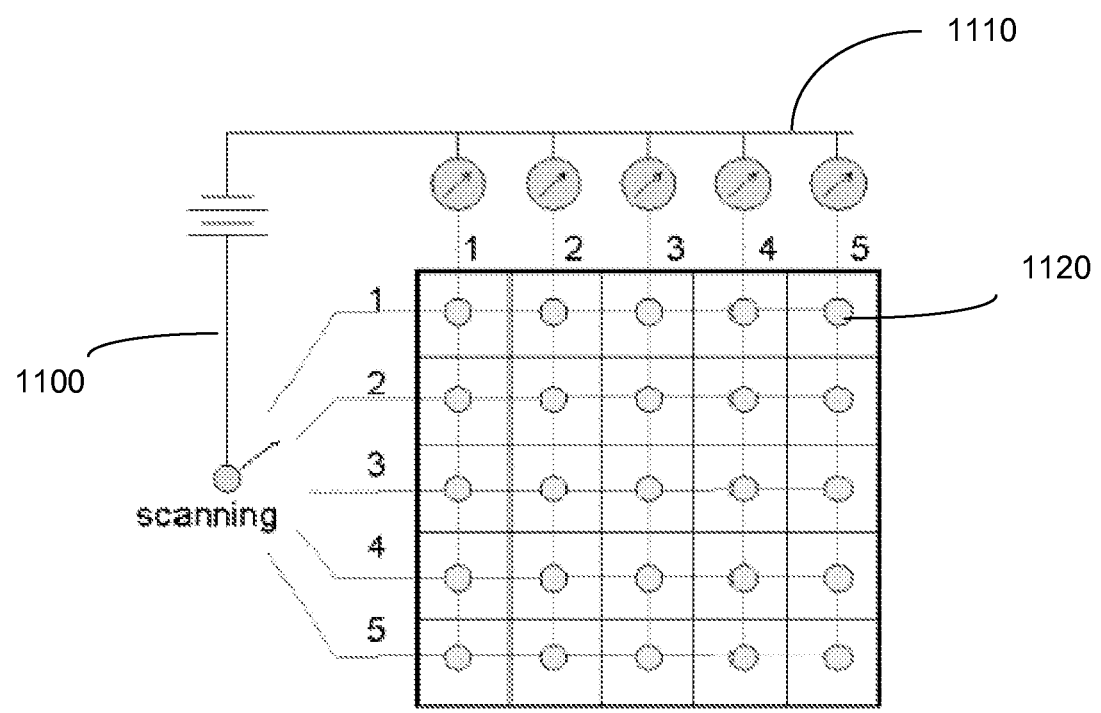
FIG. 11 schematically presents an array sensors that can be used for monitoring nucleic acid sequencing reactions.

Referring now to FIG. 11, an array of electronic sensors is shown. For simplicity, the array is shown having five rows and five columns of sensors, however the invention is not so limited and arrays can be built having a variety of dimensions and numbers of sensor regions. For example, arrays of sensors comprise from $10^2$ to as many as $10^{10}$ sensors, from $10^4$ to $10^9$, from $10^4$ to $10^8$, from $10^4$ to $10^7$, or from $10^3$ to $10^6$ sensors. In FIG. 11, the sensors are depicted as FET sensors (or extended gate FET sensors) that are connected to a source line 1100 and a drain line 1110. Reaction regions 1120 are shown in FIG. 11 having circular dimensions (a cavity), however embodiments of the present invention are not so limited and other shapes and dimensions are possible, such as for example, those having rectangular or other multisided configurations or even flat surfaces are possible. The reaction region 1120 forms part of the transistor gate. The FET sensors can be monitored individually or as a group. Additionally, an optical fluorescence imager (or a scanner) (not shown) is employed above the array to image fluorescent labels.

In general, arrays of sensors are formed in a pattern or a regular design or configuration or alternatively are randomly distributed sensors. In some embodiments, a regular pattern of sensors are used the sensors are addressed in an X-Y coordinate plane. The size of the array will depend on the end use of the array. Arrays containing from about two to many millions of different discrete sensors can be made. Very high density, high density, moderate density, low density, or very low density arrays are made. Some ranges for very high-density arrays are from about 100,000,000 to about 1,000,000,000 sensors per array. High-density arrays range from about 1,000,000 to about 100,000,000 sensors. Moderate density arrays range from about 10,000 to about 100,000 sensors. Low-density arrays are generally less than 10,000 cavities. Very low-density arrays are less than 1,000 sensors.

In general, a sensor array allows many immobilized DNA molecules to be sequenced simultaneously. The DNA molecules immobilized in the sensing regions of the array can either be a sample to be sequenced or capture DNA probes of known sequence can be first immobilized and then the sample to be sequenced can be hybridized to the immobilized probes. The capture probes have a sequence designed to hybridize to sections of the sample DNA. Alternatively, a common adaptor sequence is ligated with the DNA molecule to be sequenced and the capture probe sequence is a sequence that recognizes the common adaptor sequence. DNA density in the sensor regions is controlled by dilution. Typically, DNA fragments to be immobilized are diluted so that statistically each sensor has one DNA molecule immobilized. Information from sensors showing ambiguous results can be disregarded. Sequence information is assembled from the sensors having a single DNA molecule immobilized. Chemical information, such as for example a change in pH or in ionic concentration, from each reaction region is sensed independently. Micro and nano-structures on the array are optionally built to minimize diffusion. For example, wells can be built over or around each sensor, or the sensor well array can be placed upside down, well facing down, with the temperature in the down side lower than the chip side, and a low melting point gel (such as low melting point agarose) can be used to make the reaction mixture. Standard silicon and semiconductor processing methods allow a highly integrated sensor array to be made. For example, a 2.5×5 cm$^2$ silicon wafer chip can hold as many as 5×10$^9$ sensors that are about 0.5×0.5 μm$^2$.

In alternate embodiments, the array surface containing many sensors is uniformly modified and the end of different DNA molecules are also uniformly modified so that the DNA molecules can be chemically (through cross-linking, for example) or biochemically (through affinity binding) attached to the surface of the sensor. Density is controlled, for example, through dilution. For a large array containing millions or billions of sensors, the same DNA molecule can be in different sensors. To sequence a human genome, for example, the data typically have to be more than 10× redundant to achieve high accuracy.

Optionally some or all of the electronics for sensing and recording data are integrated circuits that are part of the substrate that house an array of electronic sensors. Electronics providing input and output control are optionally housed in the substrate, such as in an integrated circuit chip, or are provided through circuitry that is external to the substrate. An array of sensing electrodes is optionally equipped with circuitry for individually addressing the electrodes, driving the electrodes at selected voltages, memory for storing voltage current information to be supplied to the electrodes, memory and microprocessors for measuring electrode characteristics, differential amplifiers, current-sensing circuits (including variants of circuits used in CMOS image sensors), and or field effect transistors (direct and floating gate). Alternatively, one or more of these functions can be performed by external instruments and or attached computer system.

The nucleic acid sequencing methods are optionally integrated into a miniaturized device, such as a microfluidic or a nanofluidic device. Additionally, the nucleic acid sequencing methods according to embodiments of the invention are automated though the use of a computer to control the delivery of reagents and monitor the results from electrical or optical measurements, such as current flow in FETs, impedance between electrodes, redox potentials of labels, and or fluoroescence detection. Sequence data is assembled from multiple cycles of reactions. Further, the methods shown in FIGS. 2, 3, 5, and 6 can be performed in a highly parallel manner using an array of reaction regions in which one or more nucleic acid(s) to be sequenced are immobilized. Microscale fluidic devices typically have interior features for fluid flow and containment having diameters of 500 μm or less. Nanoscale fluidic devices typically have interior features for fluid flow and containment having diameters of 500 nm or less.

Persons skilled in the relevant art appreciate that modifications and variations are possible throughout the disclosure and combinations and substitutions for various components shown and described. Reference throughout this specification to "one embodiment" or "an embodiment" means that a particular feature, structure, material, or characteristic described in connection with the embodiment is included in at least one embodiment of the invention, but does not necessarily denote that they are present in every embodiment. Furthermore, the particular features, structures, materials, or characteristics may be combined in any suitable manner in one or more embodiments. Various additional structures may be included and or described features may be omitted in other embodiments.

We claim:
1. A compound having the formula,

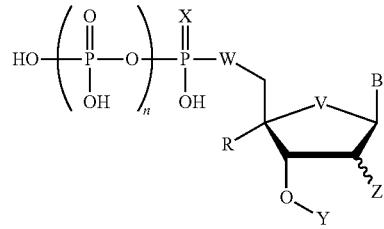

wherein X is selected from the group consisting of S, —BH, Se, and O; B is selected from the group consisting of adenine, cytosine, guanine, thymine, uracil, 2,4-difluoro-5-toluene, isoguanine, and isocytosine; W is selected from the group consisting of O, S, CH$_2$, CF$_2$, CHF, and NH; Z is selected from the group consisting of H, OH, F, SH, N$_3$, OMe, and NH$_2$; V is selected from the group consisting of O, S, Se, CH$_2$, CF$_2$, CHF, and NH; R is selected from the group consisting of H, N$_3$, NH$_2$, CH$_3$(CH$_2$)$_m$NH wherein m is a number between 0 and 9, benzylamino, AcO, MeO, hydroxymethyl, and benzyloxymethyl; Y is selected from the group consisting of azidomethyl, allyl, acetyl, and o-nitrobenzyl; and n is a number between 2 and 4; wherein either X is not O, W is not O, V is not O, or R is not H;

and salts thereof.

2. The compound of claim 1 wherein R is H and V is O.
3. The compound of claim 1 wherein R is H, V is O, and W is O.
4. The compound of claim 1 wherein R is H, V is O, and Z is H or OH.
5. The compound of claim 1 wherein R is H, W is O, and Z is H or OH.
6. The compound of claim 1 wherein W is O, V is O, and Z is H or OH.
7. The compound of claim 1 wherein X is O and W is O.
8. A compound having the formula,

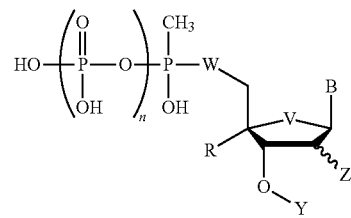

wherein B is selected from the group consisting of adenine, cytosine, guanine, thymine, uracil, 2,4-difluoro-5-toluene, isoguanine, and isocytosine; W is selected from the group consisting of O, S, CH$_2$, CF$_2$, CHF, and NH; Z is selected from the group consisting of H, OH, F, SH, N$_3$, OMe, and NH$_2$; V is selected from the group consisting of O, S, Se, CH$_2$, CF$_2$, CHF, and NH; R is selected from the group consisting of H, N$_3$, NH$_2$, CH$_3$(CH$_2$)$_m$NH wherein m is a number between 0 and 9, benzylamino, AcO, MeO, hydroxymethyl, and benzyloxymethyl; Y is selected from the group consisting of azidomethyl, allyl, acetyl, and o-nitrobenzyl; and n is a number between 2 and 4;

and salts thereof.

9. The compound of claim 1 wherein R is H and V is O.

10. The compound of claim 1 wherein R is H, V is O, and W is O.

11. The compound of claim 1 wherein R is H, V is O, and Z is H or OH.

12. The compound of claim 1 wherein R is H, W is O, and Z is H or OH.

13. The compound of claim 1 wherein W is O, V is O, and Z is H or OH.

14. The compound of claim 1 wherein W is O.

\* \* \* \* \*